(12) United States Patent
Ehrling et al.

(10) Patent No.: US 10,914,715 B2
(45) Date of Patent: Feb. 9, 2021

(54) ANALYSIS DEVICE AND METHOD

(71) Applicant: Analytik Jena AG, Jena (DE)

(72) Inventors: Christiane Ehrling, Ilmenau (DE); Heiko Henneberg, Plaue (DE); Robert Knöfel, Ilmenau (DE); Kristin Scheide, Ilmenau (DE)

(73) Assignee: Analytik Jena AG, Jena (DE)

( * ) Notice: Subject to any disclaimer, the term of this patent is extended or adjusted under 35 U.S.C. 154(b) by 224 days.

(21) Appl. No.: 15/777,656

(22) PCT Filed: Oct. 19, 2016

(86) PCT No.: PCT/EP2016/075098
§ 371 (c)(1),
(2) Date: May 19, 2018

(87) PCT Pub. No.: WO2017/084825
PCT Pub. Date: May 26, 2017

(65) Prior Publication Data
US 2019/0086376 A1   Mar. 21, 2019

(30) Foreign Application Priority Data
Nov. 19, 2015 (DE) .......................... 10 2015 120 095

(51) Int. Cl.
  *G01N 33/00* (2006.01)
  *G01N 21/3504* (2014.01)
  *G01N 31/12* (2006.01)
(52) U.S. Cl.
  CPC ..... *G01N 33/0009* (2013.01); *G01N 21/3504* (2013.01); *G01N 31/12* (2013.01)
(58) Field of Classification Search
  None
  See application file for complete search history.

(56) References Cited

U.S. PATENT DOCUMENTS 5,069,220 A  * 12/1991  Casparie ............... A61B 5/083
                                                        600/532

FOREIGN PATENT DOCUMENTS

CN     104634770 A     5/2015
CN     104713768 A     6/2015
(Continued)

OTHER PUBLICATIONS

International Search Report for PCT Application No. PCT/EP2016/075098, WIPO, dated Dec. 20, 2016, 13 pp.
(Continued)

*Primary Examiner* — Daniel S Larkin
(74) *Attorney, Agent, or Firm* — Mark A. Logan; Endress+Hauser (USA) Holding Inc.

(57) ABSTRACT

The invention relates to an analysis device for determining a measurement variable based on the concentration of one or more contents of a sample, comprising: a digestion reactor with a gas inlet and a gas outlet; a measuring device which is connected to the gas outlet of the digestion reactor; a control and analysis device which is designed to receive and process measurement values that are registered by the measuring device and are based on the measurement variable; an oxygen generating device; and a gas line system which connects the oxygen generating device to the gas inlets of the digestion reactor in order to supply oxygen generated by the oxygen generating device to the digestion reactor, wherein the gas line system comprises a gas storage device which has at least one chamber with a variable volume for receiving an oxygen quantity to be stored.

26 Claims, 3 Drawing Sheets

(56) References Cited

FOREIGN PATENT DOCUMENTS

| | | |
|---|---|---|
| DE | 69228519 T2 | 10/1999 |
| DE | 102008013754 A1 | 9/2009 |
| DE | 202012102724 U1 | 8/2012 |
| DE | 202013105594 U1 | 9/2014 |
| EP | 0052988 B1 | 9/1986 |
| EP | 0989401 A2 | 3/2000 |
| JP | 2007098308 A | 4/2007 |

OTHER PUBLICATIONS

Search Report for German Patent Application No. 10 2015 120 095.3, German Patent Office, dated Sep. 6, 2016, 6 pp.

\* cited by examiner

ANALYSIS DEVICE AND METHOD

CROSS-REFERENCE TO RELATED APPLICATIONS

The present application is related to and claims the priority benefit of German Patent Application No. 10 2015 120 095.3, filed on Nov. 19, 2015 and International Patent Application No. PCT/EP2016/075098, filed on Oct. 19, 2016 the entire contents of which are incorporated herein by reference.

TECHNICAL FIELD

The invention relates to an analysis device for the determination of a measurement variable dependent upon the concentration of one or more constituents of a sample.

BACKGROUND

Such a measurement variable can, for example, be a concentration of one or more substances, or an element such as sulfur, chlorine, or hydrogen in the sample, or a cumulative parameter such as the total organically-bound carbon content (total organic carbon, abbreviated TOC), total carbon content (organically- and inorganically-bound, abbreviated TC) or the total bound nitrogen (total nitrogen, abbreviated $TN_b$).

Known analytical devices for automatically determining such measurement variables comprise a digestion reactor into which a solid, liquid, or gaseous sample is metered. In the digestion reactor—which, for example, can be designed as a pyrolysis tube—the sample contents are thermally digested. The organically- and inorganically-bound carbon is converted into carbon dioxide $CO_2$, nitrogen is converted into nitrogen oxide $NO_x$, sulfur is converted into sulfur oxides $SO_2/SO_3$, chlorine is converted into hydrogen chloride, and HCl and hydrogen are converted into water $H_2O$. The resulting gas or gas mixture, with the assistance of a carrier gas that permanently flows through the digestion reactor, which generally also delivers the oxygen required for the reaction, is fed through a drying and absorber device of a measuring device that serves to determine the measurement variable.

In some applications—in particular, for analysis within the trace range—highly pure oxygen is used as the reaction and carrier gas. The measuring device comprises one or more specific detectors that serve to determine the portion of the oxidation products which is relevant for the measurement variable to be determined that is in the carrier gas stream fed to the detector. If, for example, the TOC value of the sample is to be ascertained, an infrared detector serves as the specific detector, which infrared detector determines the $CO_2$ content in the carrier gas stream, and from which a measurement value of the TOC value of the sample can be derived. To determine the $TN_b$, an $NO_x$ content of the gas stream can be determined by means of a chemical luminescence measurement.

Oxygen as a carrier gas or as a reaction partner for thermal digestion of the samples is normally provided to conventional analysis devices via pressurized gas cylinders, gas generators, or by means of adsorbents. The disadvantage of this method is the required level of cost and equipment, as well as the low degree of purity of the oxygen when adsorbents are used.

From DE 20 2012 102 724 U1, an analysis device with a thermal digestion system has become known that comprises a device for directly generating oxygen from ambient air. A ceramic material with a perovskite structure serves for this purpose that, for example, can be designed as a membrane or granules, and that exhibits oxygen ion conductivity at high temperatures. This oxygen ion conductivity makes it possible to separate the oxygen from the other components in the ambient air by oxygen being selectively transported through the ceramic material. To heat the ceramic material to the temperature necessary to transport oxygen, the process heat of the thermal digestion system is used in the analysis device described in DE 20 2012 102 724 U1.

The amount of oxygen needed to operate the analysis device may fluctuate over the operating time of the analysis device. For example, in addition to the digestion system, the analysis device may comprise further oxygen consumers that require oxygen discontinuously, i.e., only during certain operating phases. For example, an analysis device for determining TOC can have a device for separating and/or determining the inorganically-bound carbon that is designed to blow out the inorganically-bound carbon with oxygen from the acidified sample before the digestion.

In the elementary analysis, the sample is preferably fed only the amount of oxygen in a carrier gas stream that is needed for thermal digestion of the compounds of the element to be detected that are contained in the sample. In this case, it is desirable to be able to control the added amount of oxygen as precisely as possible.

The oxygen-generating device described in DE 20 2012 102 724 U1 typically provides a constant amount of oxygen as, basically, a function of time. This results from the dimensions of the ceramic material used for generating oxygen and the operating temperature of the device. To ensure that a sufficient amount of oxygen is available to the analysis device at all times, the ceramic material must be dimensioned so that the maximum required amount of oxygen is continuously available—if necessary, with an additional safety margin. On the other hand, it is desirable to design the oxygen-generating device as compactly as possible, and to keep the required amount of ceramic material as low as possible.

SUMMARY

The aim of the invention is to develop the analysis device known from the prior art such that the oxygen-generating device can be designed in a manner that is compact and saves material.

The analysis device according to the invention for the determination of a measurement variable dependent upon the concentration of one or more constituents of a sample comprises:

a digestion reactor with a gas inlet and a gas outlet;

a measuring device that is connected to the gas outlet of the digestion reactor;

a control and analysis device that is designed to receive and process measurement values that are registered by the measuring device and depend upon the measurement variable;

an oxygen-generating device; and a gas line system that connects the oxygen-generating device to the gas inlet of the digestion reactor in order to supply oxygen generated by the oxygen-generating device to the digestion reactor, wherein the gas line system comprises a gas storage device that has at least one chamber, with a variable volume, that serves for receiving an amount of oxygen to be stored.

The gas storage device serves for receiving the oxygen generated continuously by the oxygen-generating device. The oxygen-holding capacity of the gas storage device is advantageously adjusted to the amount of oxygen generated per time unit such that, in analysis device operating phases during which the currently-generated amount of oxygen is not completely consumed, it can store an amount of oxygen that is large enough for a sufficient amount of oxygen to be available in operating phases in which more than the currently-generated amount of oxygen is required. In this manner, it is possible to compactly design the oxygen-generating device, and, in particular, the material, which serves to generate oxygen, of the oxygen-generating device.

In one embodiment, the gas line system comprises a control device for regulating the flow of at least one oxygen stream flowing through the gas line system from the gas storage device to the digestion reactor.

A gas feed line can terminate in the chamber of the gas storage device and be connected to a gas outlet of the oxygen-generating device—in particular, via a pump—wherein the chamber has a gas outlet that is connected to the gas inlet of the digestion reactor—in particular, via the control device.

In another embodiment, the gas line system additionally connects the oxygen-generating device via the gas storage device to one or more additional consumers, in order to supply them with oxygen generated by the oxygen-generating device, and wherein the control device for regulating flow is additionally designed to control transport of oxygen through the gas line system from the gas storage device to the one or more additional consumers.

An additional consumer can, in the case in which the analysis device is a device for determining the parameter TOC, be a device for removing inorganically-bound carbon.

The gas outlet of the at least one chamber of the gas storage device can be connected via the control device to the one additional consumer, or to one or more—in particular, to each—of the additional consumers.

In one embodiment, in which a gas feed line terminates in the chamber and is connected to a gas outlet of the oxygen-generating device, the chamber can comprise a wall region that is designed to be deflected against a restoring force when the amount of oxygen contained in the chamber increases while enlarging the volume of the chamber. In this embodiment, oxygen storage is possible by deflecting the wall region. When more oxygen is removed from the chamber by means of the control device for regulating flow, the deflected wall region is moved back into its original position by the restoring force, with a decrease in the volume of the chamber. In this embodiment, no other means, such as drives, are needed to actively enlarge or decrease the chamber volume for receiving or discharging oxygen.

The gas storage device can, for example, be formed by a cylinder closed on one side by a floor, and a piston that can move axially in the cylinder relative to the cylinder axis, wherein the axial position of the piston depends upon the amount of oxygen contained in the chamber. The piston can seal the cylinder gas-tight on its side opposite the floor. For example, the piston can be guided gas-tightly within the cylinder. It is also possible for the piston to be joined gas-tightly to the wall of the cylinder by means of a bellows or a flexible membrane, such that the cylinder is sealed gas-tight, and axial movement of the piston is simultaneously guaranteed. In this embodiment, the weight acting on the piston serves as a restoring force against which the piston is deflected while enlarging the chamber volume. If the piston is connected by means of a membrane or a bellows to the cylinder wall, the elasticity of the membrane or the bellows also can generate a restoring force that acts on the piston, alternatively or in addition to the weight of the piston.

The gas line system can comprise means for monitoring the deflection of the wall region of the chamber—in particular, the axial position of the piston. Such means can, for example, be proximity switches, light barriers, image-processing sensors, or position sensors that output their measuring signals, which correlate with the axial position of the piston, to the control and analysis device. The axial position of the piston can be converted into an amount of oxygen stored in the chamber. Monitoring the axial position of the piston therefore makes it possible to check whether an amount of oxygen needed for this operating phase is available, before an operating phase of the analysis device starts.

The control and analysis device of the analysis device can be designed to receive the measuring signals representing the axial position of the piston, and to ascertain therefrom the amount of oxygen currently contained in the gas storage. On this basis, it can start a processing phase of the analysis system with an increased oxygen requirement, or it can delay said processing phase if the amount of oxygen in the gas storage is insufficient.

In order to be able to store a greater amount of oxygen, the gas storage device in this embodiment can also have several such similarly-designed chambers. In this case, each of the chambers can be connected via a controllable valve device to the gas outlet of the oxygen-generating device.

In an alternative embodiment, the gas storage device can have at least two chambers whose volumes are changeable by means of a control, wherein a gas feed line terminates in each of the chambers and can be connected to the gas outlet of the oxygen-generating device, and wherein each of the chambers has a gas outlet that is connected—in particular, via the control device for regulating flow—to the gas inlet of the digestion reactor, and/or, if applicable, to other available consumers. In this embodiment, the volume of the chambers can be actively changed by means of the control, which allows a regulated overpressure or underpressure to be adjusted in the chambers. By means of the adjustable overpressure or underpressure in the chambers, a flow of the oxygen transported into the chambers or removed from the chambers can be adjusted. This can, for example, be used to meter a given amount of oxygen, and to supply a consumer or the digestion reactor.

In this embodiment, each of the gas feed lines can be connected via a valve assembly to the gas outlet of the oxygen-generating device, wherein the valve assembly is designed to selectively block or release gas lines running from the gas outlet of the oxygen-generating device to the chambers—in particular, alternatingly, or according to a sequence specified by the control.

The at least two chambers can each be formed by a cylinder closed on one side by a floor, and a piston that can move axially in the cylinder relative to the cylinder axis, wherein each piston is connected to a drive that, in particular, is actuatable by the control and produces an axial movement of the piston. The piston can seal the respective cylinder gas-tight on its side opposite the floor; for example, it can be guided gas-tightly within the cylinder. It is also possible for the piston to be joined gas-tightly to the wall of the cylinder by means of a bellows or a flexible membrane, such that the cylinder is sealed gas-tight, and axial movement of the piston is simultaneously guaranteed.

In this embodiment, the gas storage device can comprise pressure sensors that are designed to detect the pressure predominating in the chambers, and to output corresponding pressure measuring signals to the control and analysis device of the analysis device. With reference to the predominating pressure in the chambers, the control and analysis device can determine the amount of oxygen currently stored in the chambers. The control and analysis device can be advantageously designed to start operating phases of the analysis device that have an elevated oxygen demand only when there is a sufficient amount of oxygen in the gas storage device.

The control and analysis device of the analysis device can be designed to control the analysis device—in particular, the control device for regulating flow, the valve assembly, and/or the volume of the chambers of the gas storage device—for performing measurements for determining the measurement variable. In addition, the control and analysis device of the analysis device can be designed to control the analysis device for performing diagnostic or maintenance procedures. It can be designed as a central, electronic data processing device of the analysis device. In an alternative embodiment, the control and analysis device can also be formed from several, spatially separate, individual electronic data processing devices that are, however, linked to each other for communication.

The aforementioned measuring device of the analysis device comprises at least one detector specifically for recording the contents of one or more given compounds, such as $CO_2$ or $NO_x$, in a gas stream leaving the digestion reaction reactor via the gas outlet. For example, the analysis device can comprise, as a detector specifically for determining a TOC value, an infrared detector that is designed to generate a measuring signal dependent upon the $CO_2$ content of the gas stream. Alternatively or in addition, the analysis device can comprise a chemical luminescence detector (CLD detector) as a detector specifically for determining a $TN_b$ value. The detector specifically for determining the $TN_b$ value can also be designed to generate a measuring signal based upon infrared detection or an electrochemical measurement. If the analysis device is an elemental analysis device, the measuring device can comprise a detector specific to the element to be determined, such as carbon, sulfur, nitrogen, hydrogen, and/or chlorine. Such detectors are known per se in the prior art.

The oxygen-generating device can comprise one or more oxygen-permeable membrane tubes, which are closed on one side and consist of a ceramic material with a perovskite structure, that have a retentate side facing the reaction chamber, and a permeate side facing away from the inside of the tubes. If a lower oxygen partial pressure predominates on the permeate side, above a minimum operating temperature of the membrane tubes, oxygen from air fed to the permeate side is transported through the membrane into the interior of the membrane tubes. To achieve the minimum operating temperature, a heating device of the digestion system is used.

The invention also comprises a method for determining a measurement variable that depends upon the concentration of one or more contents of the sample—in particular, by means of an analysis device in accordance with one of the embodiments described above—with the steps of:

continuously generating a substantially constant amount of oxygen per time unit by means of an oxygen-generating device;

transporting the generated oxygen into a gas storage device that has at least one chamber, with a variable volume, that serves for receiving an amount of oxygen to be stored;

removing a currently-required amount of oxygen from the gas storage device and transporting the removed amount of oxygen to the digestion reactor, and/or to one or more additional consumers;

performing a digestion of the sample in the digestion reactor, and introducing, into the digestion reactor, oxygen removed from the gas storage device;

recording a measurement value, dependent upon the measurement variable, in a gas stream discharged from the digestion reactor.

The method according to the invention can, moreover, comprise the following step:

transporting the generated oxygen into the chamber by means of a pump, wherein a wall region of the chamber is deflected against a restoring force when the amount of oxygen contained in the chamber increases while enlarging the volume of the chamber, such that a volume of the generated oxygen that depends upon a delivery rate with which the generated oxygen is transported is stored in the chamber under a pressure determined by the restoring force.

The chambers of the gas storage device can be formed by a cylinder closed on one side by a floor, and a piston that can move axially in the cylinder relative to the cylinder axis and seals the cylinder on its side opposite the floor, wherein the generated oxygen is transported—in particular, by means of a pump—into the chamber at a delivery rate such that a volume of the generated oxygen that depends upon the delivery rate is stored in the chamber under a pressure determined by the weight of the piston and cross-section of the cylinder.

The removal of the currently-required amount of oxygen can be controlled and/or regulated on the basis of a degree of deflection of the aforementioned deflectable wall region of the chamber—in particular, by the axial position of the piston.

If, in an alternative embodiment, the gas storage device comprises at least two chambers whose volumes can be changed by means of a control, the method according to the invention can also alternatively comprise the steps of:

transporting the generated oxygen into the first of the two chambers while enlarging the volume of the chamber until a given volume and a given control pressure are reached in the chamber;

after the given volume and given control pressure in the first chamber are reached, removal of the currently-required amount of oxygen from the first chamber.

In this version of the method, the oxygen generated by the oxygen-generating device can be transported into the other, second chamber of the at least two chambers during the removal of the currently-required amount of oxygen from the first chamber. This allows the two chambers to be alternatingly filled and emptied.

The method can be performed fully automatically by means of the control and regulating device of the analysis device.

BRIEF DESCRIPTION OF THE DRAWINGS

The invention is explained in further detail below on the basis of the exemplary embodiments shown in the figures. In the figures.

DETAILED DESCRIPTION

Figure 1:
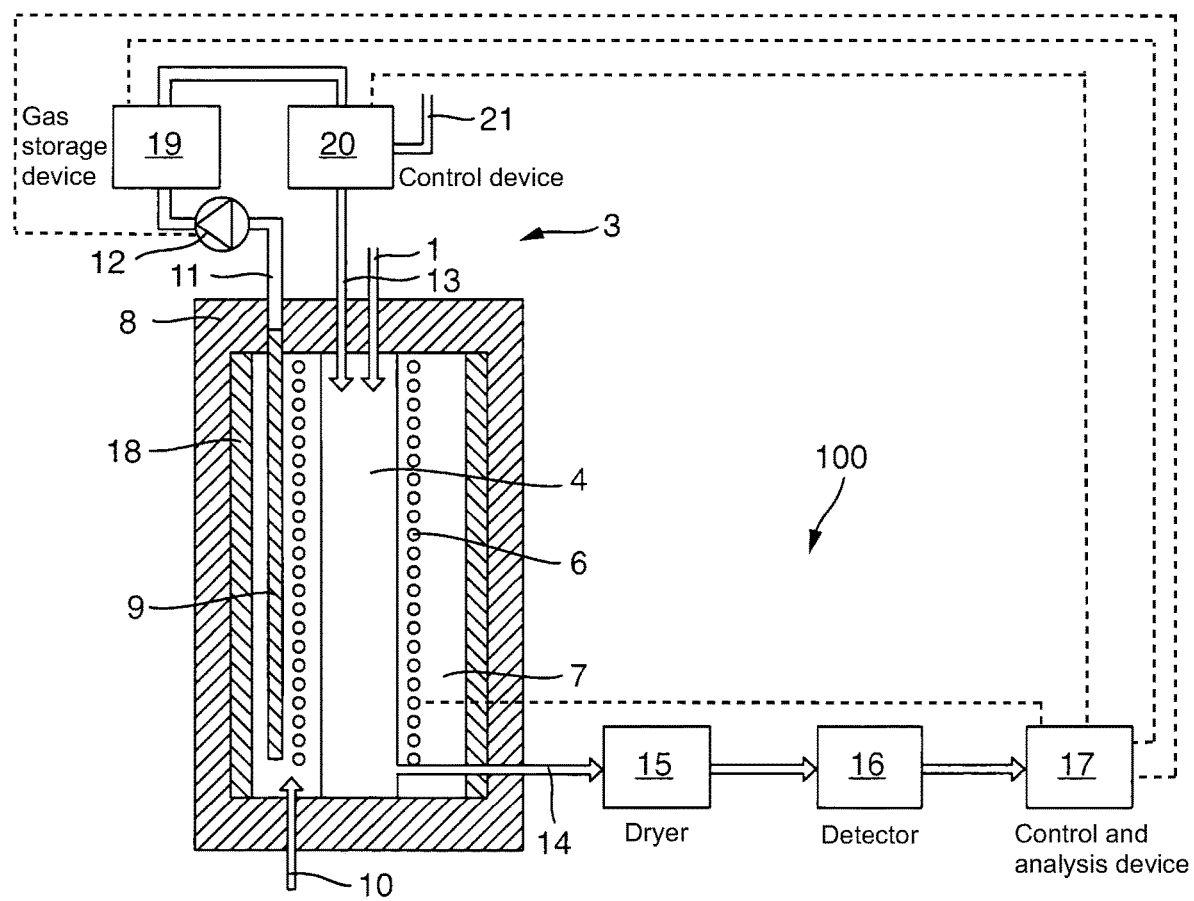
FIG. 1 shows a schematic representation of an analysis device.

The analysis device 100 schematically portrayed in FIG. 1 has a sample dosing system 1 by means of which a sample of a substance to be investigated can be fed to a thermal digestion system 3. The digestion system 3 comprises a tubular digestion reactor 4 that can be heated by means of a heating device 6. The heating device 6 in the present example is designed as an electric resistance heater that comprises a heating conductor which spirals around the digestion reactor. The digestion system 3 is accommodated in a housing 8 in which are also arranged an oxygen-generating device with several oxygen-permeable membranes 9 (for the sake of clarity, only one membrane is shown in FIG. 1) and a supply gas line system 7 (not shown in detail in FIG. 1) surrounding the digestion reactor 4. The digestion reactor 4, the heating device 6, and the feed gas line system 7 are thermally insulated from the housing 8 by means of the surrounding insulating tube 18.

The membranes 9 in the present example are designed as tubes formed from a ceramic material with oxygen ion conductivity. Suitable ceramic materials are, for example, oxides with a perovskite structure. Perovskites are ternary oxides with an $ADO_3$-type lattice structure. Above a material-dependent minimum operating temperature that can lie between 500 and 1,000° C., these materials simultaneously possess electrical conductivity and oxygen ion conductivity. It is therefore possible to transport oxygen through a gas-tight ceramic membrane, wherein the oxygen is separated from the other components of a feed gas—that can, for example, be air—fed to the membrane. If a higher oxygen partial pressure predominates on the outside of the tubes (also termed the retentate side) than on the inside facing the interior of the tubes (also termed the permeate side), at temperatures above the minimum operating temperature of the membrane, oxygen molecules are reduced on the retentate side to negatively-charged oxygen ions, oxygen ions are transported through the membrane from the retentate side to the permeate side, and oxygen ions are oxidized to molecular oxygen on the permeate side. In this manner, oxygen is transported through the membrane and is separated from the remaining components of the feed gas on the retentate side.

Suitable materials are, for example, perovskite-like oxides such as $Ba_{1-x}Sr_xCo_{1-y}Fe_yO_{3-\delta}$—especially, for example, $Ba_{0.5}Sr_{0.5}Co_{0.8}Fe_{0.2}$—or $La_{1-x}Sr_xCo_{1-y}Fe_y$, $O_{3-\delta}$—especially, for example, $La_{0.2}Sr_{0.8}Co_{0.5}Fe_{0.5}O_{3-\delta}$—as well as nickel/cobalt perovskite oxide with the composition $La_{0.5}Sr_{0.5}Co_{0.8}Ni_{0.2}O_{3-\delta}$.

The membranes 9 designed as tubes are sealed at one end. Their opposite ends are connected via a gas line 11 to a pump 12 that is designed to generate an underpressure in the interior of the tubes so that, between the retentate side and permeate side, the oxygen partial pressure gradient that is necessary for transporting oxygen arises. In the example portrayed here, air from the surroundings of the analysis device 100 is introduced as a feed gas, via the inflow channel 10, into the feed gas line system 7. There can also be several inflow channels; here, only one inflow channel is portrayed, for the sake of clarity.

The analysis device 100 does not need or use any additional heater or heat exchanger for heating the membranes 9 to a temperature above the minimal operating temperature. The heating device 6 serving to heat the digestion reactor 4 simultaneously serves to heat the membranes 9.

By means of the pump 12, the gaseous oxygen arising on the permeate side of the membranes 9 is conducted into a gas storage device 19. By means of a control device 20 for regulating flow, a currently-required amount of oxygen can be removed from the gas storage device 19 as needed and introduced via the gas inlet 13 into the digestion reactor 4, or can be fed via another gas line 21 to other oxygen consumers of the analysis device. In the present example, the oxygen simultaneously serves as a carrier gas and as an antioxidant for the constituents of the sample introduced into the digestion reactor via the sample dosing system 1. The control device 20 is therefore designed to continuously maintain a given gas stream through the digestion reactor. The control device 20 comprises a gas line and valve system, as well as an electronic control circuit that is designed to actuate the valve system.

The sample is digested at a temperature between 500 and 1,000° C., which is achieved by means of the heating device 6. In addition to the gas inlet 13, the digestion reactor 4 also has a gas outlet 14 that connects the digestion reactor 4 to a dryer 15. The dryer 15 is connected via a gas line to a detector 16 which is designed to output a measuring signal that depends upon the measurement variable to be determined. In the present example of a TOC analysis device, the detector 16 can be an infrared detector that is designed to generate a measuring signal that depends upon the $CO_2$ content of the gas stream fed from the gas outlet 14 via the dryer 15 to the detector 16. The detector 16 is connected to a control and analysis device 17 which is designed to detect the measuring signal of the detector 16 and to determine the measurement variable—here, the TOC value of the sample—on the basis of the measuring signal. The control and analysis device 17 can, for example, be an electronic data processing device—in particular, a PC—that comprises and can execute an evaluation program serving to determine the measurement variable.

The control and analysis device 17 also serves to control the analysis device 100, in addition to evaluating the measuring signals. It is designed to control the heating device 6, the pump 12, any available drives of the gas storage device 19, and the control device 20 for regulating flow. The control and analysis device 17 can be designed in the form of a single, central data processing device. Alternatively, it can comprise several individual data processing devices which may be spatially separate from each other and each control individual components of the analysis device or gas storage device, and are linked to each other for communication.

The overall area of the membrane tubes 9 for generating oxygen is designed to continuously provide an oxygen stream between 50 $cm^3$ to 5 $dm^3$/min (50 mL to 5 L/min). However, the analysis device 100 is designed such that an overall maximum of oxygen that is required by the digestion reactor 4 and the other oxygen consumers in certain operating phases can exceed the amount of oxygen generated by the oxygen-generating device during these operating phases. The gas storage device 19 is designed to temporarily store the unnecessary excess oxygen in operating phases in which the digestion reactor 4 and the other oxygen consumers jointly require less than the amount of oxygen generated during these operating phases by the oxygen-generating device. The stored oxygen is available in operating phases in which the overall required amount of oxygen exceeds the amount of oxygen generated during these operating phases by the oxygen-generating device. The gas storage device is designed so that the amount of oxygen required for the current operating phase and an additional safety surplus, which, for example, can be about 10%, are always available.

It is also possible to design the control and analysis device 17 to control the performance of measuring cycles of the analysis device 100 such that, before an operating phase with an elevated amount of oxygen, i.e., exceeding the amount of oxygen continuously made available by the oxygen-generating device, it is initially checked whether a sufficient amount of additional oxygen is stored in the gas storage device, and the start of the operating phase is delayed until a sufficient amount of oxygen is present in the gas storage device.

Figure 2:
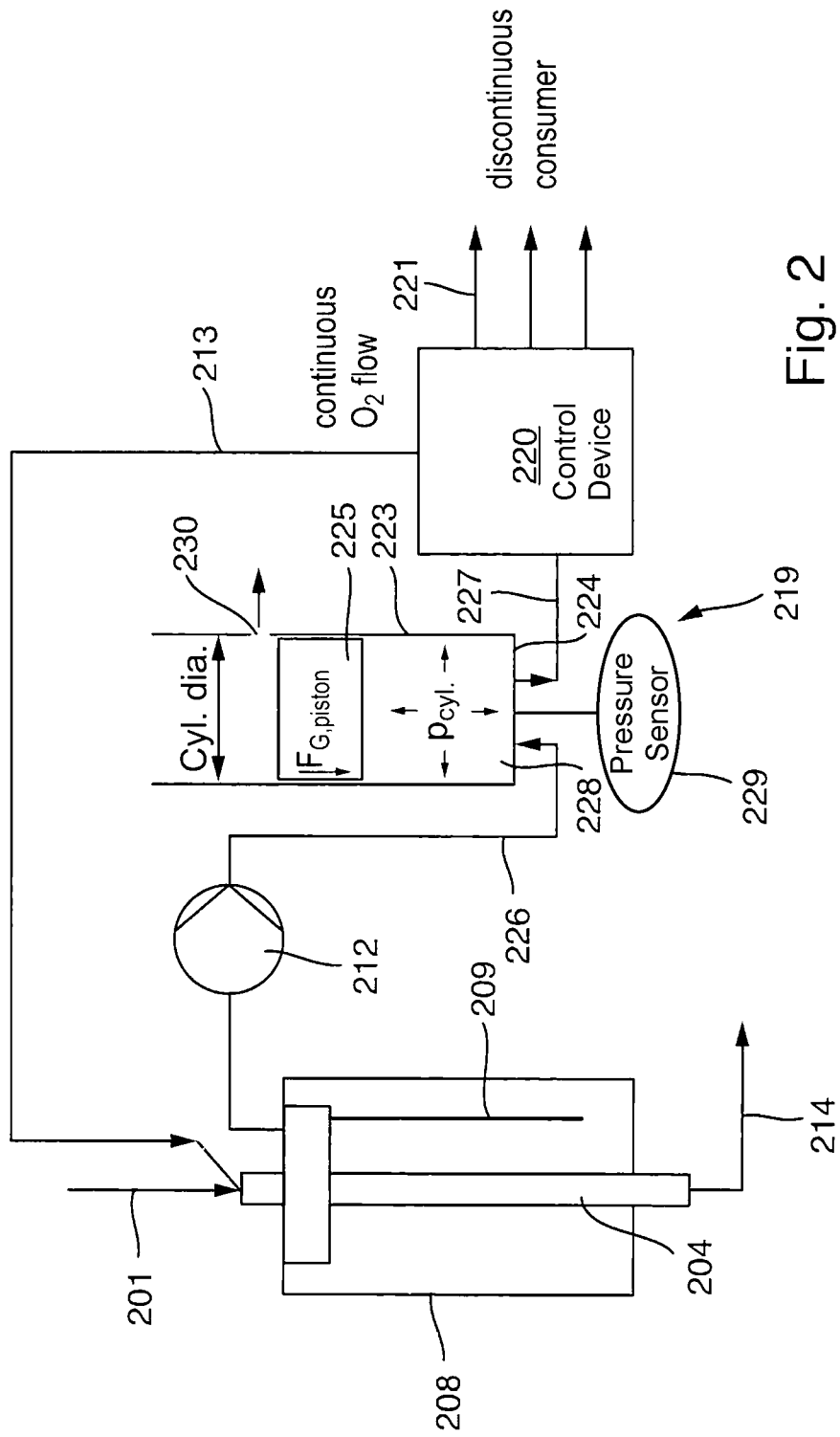
FIG. 2 shows a schematic representation of a first exemplary embodiment of a gas storage device for an analysis device.

FIG. 2 schematically portrays a first exemplary embodiment of a gas storage device 219 of an analysis device. The analysis device 100 is basically designed like the analysis device described with reference to FIG. 1. In particular, it comprises a heatable digestion reactor 204 that is accommodated in a housing 208 and can be fed a sample for analysis via a sample feed 201. Moreover, the analysis device comprises an oxygen-generating device with membrane tubes 209 that serve to generate oxygen from the ambient air. The inner permeate side of the membrane tubes 209 is connected via a vacuum pump 212 to the gas storage device 219.

The gas storage device 219 comprises a cylinder 223 that is sealed on one side by a floor 224. A piston 225 is movably guided axially in the cylinder relative to the cylinder axis and seals the cylinder gas-tight in the exemplary embodiment shown here. The tubular cylinder wall, the floor 224, and the piston 225 enclose a chamber 228 in which terminate a gas feed line 226, connected via the vacuum pump 212 to the oxygen-generating device, and a gas discharge line 227 that is connected to the control device 220 for flow control. The gas storage device 219 can moreover comprise a pressure sensor 229 that is designed to detect the gas pressure predominating in the chamber 228. Another gas outlet 230 terminates in the cylinder wall in a top region, in the example described here.

The control device 220 is designed basically like the control device 20 of the analysis device 100 portrayed in FIG. 1. It is connected via a gas line system 213 to the digestion reactor 204 and other consumers 221. The control device 220 comprises an electronic control circuit and a valve device that can be actuated by means of the control circuit. By controlling the valve device, the control device 220 can supply an oxygen stream coming from the chamber 228 to the digestion reactor 204 via the feed line 213, and/or two additional consumers via the feed lines 221.

The chamber 228 of the gas storage device 219 has a variable volume due to the axial mobility of the piston 225. This storage volume is designed such that it can receive approximately the delivery volume of the delivered oxygen generated by the oxygen-generating device over 3 to 30 min. By means of the pump 212, the piston 225 is displaced by the oxygen introduced into the chamber against its weight acting as a restoring force, wherein a constant pressure differential from the surrounding atmosphere accumulates. The pressure differential is determined by the weight and area of the piston 225. Disregarding the friction arising from the axial movement of the piston 225, the pressure $p_{cyl}$ in the chamber 228 is:

$$p_{cyl} = \frac{4}{\pi} \cdot \frac{F_{G,piston}}{\phi_{cyl}^2},$$

where $F_{G,piston}$ is the weight of the piston, and $\phi_{cyl}$ is the cylinder diameter.

This constant overpressure serves to regulate the flow of the main gas stream to the digestion reactor 204, and the auxiliary gas streams to the other consumers. The use of other pressure regulators and control valves is therefore unnecessary. It is sufficient for the pump 212 to generate a slight overpressure of, for example, 20 to 100 hPa (20 to 100 mbar) for the storage system, in addition to the system-related underpressure in the delivery system serving to transport oxygen. If the amount of oxygen available in the chamber 228 increases strongly enough to lift the piston 225 above the level of the gas outlet 230, oxygen escapes into the surroundings, which leads to a downward movement of the piston 225. This ensures that the volume of the chamber 228, and hence the stored amount of oxygen, does not exceed a maximum value established by the position of the gas outlet 230.

The storage volume which can be varied by the movement of the piston 225 ensures a very low dead volume of the gas storage device 219.

A method for storing oxygen in the gas storage device 219 and a method for operating the gas storage device 219 that always supplies the digestion reactor 204 and other consumers with oxygen is described below:

The analysis device that runs measuring cycles to determine the measurement variable or waiting period is controlled by a control and analysis device that can be designed in the same way as the control and analysis device 17 of the analysis device 100 described with reference to FIG. 1. The measuring cycles can be divided into individual operating phases. In each operating phase, the control device 220 supplies the digestion reactor 204, and, as needed, one or more additional consumers, with the amount of oxygen required in this operating phase. In the process, the oxygen is removed from the chamber 228. The control device can receive corresponding control commands for this from the control and analysis device, with which it is linked for communication. Alternatively, the aforementioned control circuit of the control device 220, which control circuit actuates the valve device of the control device 220, can be a component of the control and analysis device of the analysis device.

To ensure that, at the beginning of a processing cycle or an operating phase, there is a sufficient gas reserve for processing a pending sequence of operating phases of the analysis device, the axial position of the piston 225 can be monitored by means of suitable sensors. The corresponding sensor signals can be processed by the control and analysis device of the analysis device. If it is determined that the currently existing gas reserve is insufficient, the reserve can be filled up by pausing the process. Preferably, the process is paused only at a time at which such a pause would not endanger the procedure being carried out by the analysis device.

Figure 3:
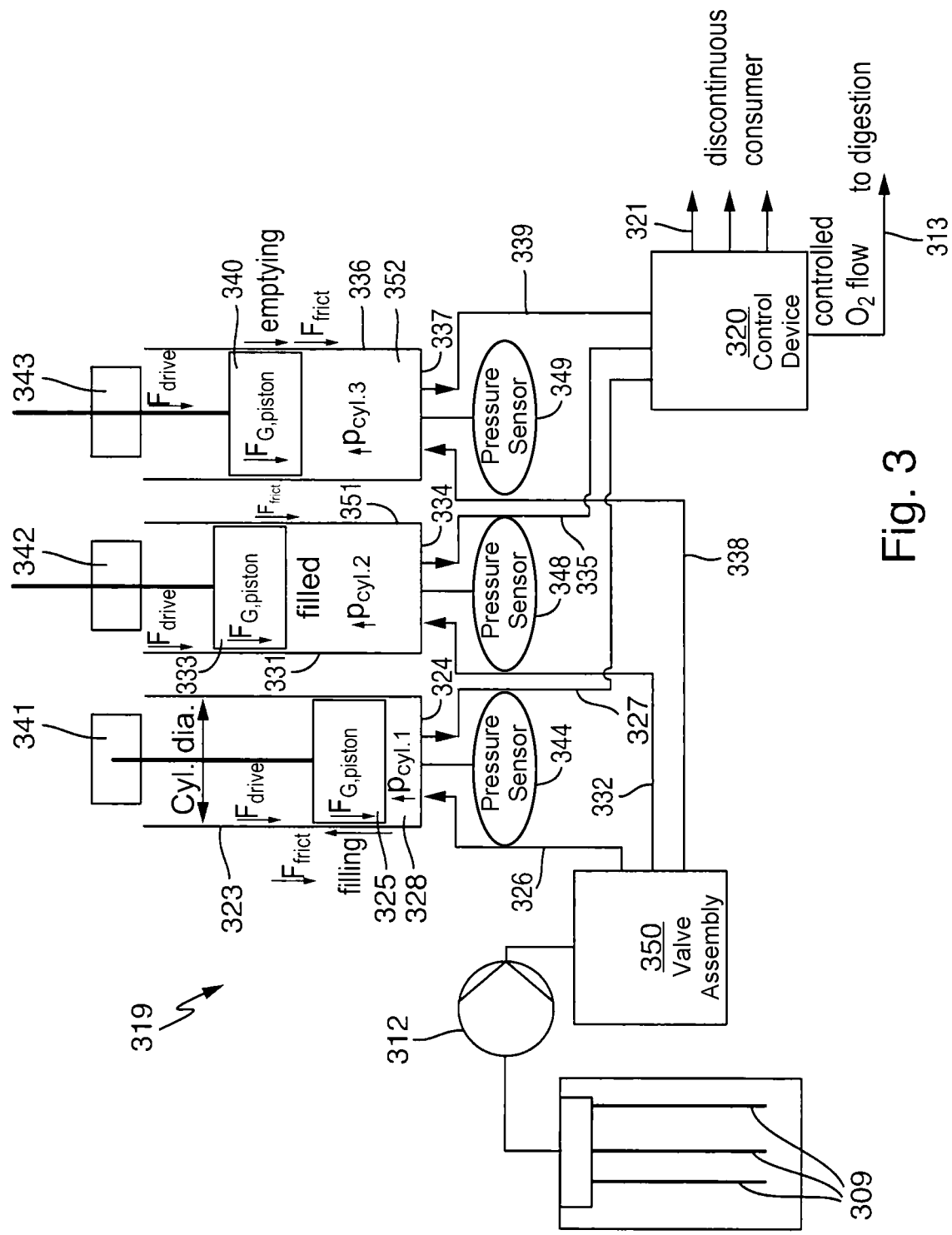
FIG. 3 shows a schematic representation of a second exemplary embodiment of a gas storage device for an analysis device.

FIG. 3 shows a further exemplary embodiment of a gas storage device 319. This can be used in an analysis device that has other oxygen consumers in addition to a digestion reactor, and that comprises an oxygen-generating device which is designed to generate oxygen from the ambient air. For example, use of the gas storage device 319 in the analysis device described with reference to FIG. 1 may be considered.

The oxygen-generating device has several membrane tubes 309 that, according to the principle described above in conjunction with FIG. 1, continuously generate highly pure oxygen. The permeate side of the membrane tube is connected via a vacuum pump 312 to a gas line system and a valve assembly 350 that serve to selectively supply, as needed, the oxygen generated by the oxygen-generating device to one of three chambers 328, 351, 352 of the gas storage device 319, which each have a variable volume.

In the example presented here, the gas storage device 319 comprises three cylinders 323, 331, 336 that are each closed on one side by a floor 324, 334, 337, and in each of which a piston 325, 333, 340 is guided in an axially-movable manner. The chambers 328, 351, 352 are each formed by the tubular cylinder wall, the floor 328, 334, 337, and the piston 325, 333, 340 that seals the chambers 328, 351, 352 gastight. One feed line 326, 332, 338 and one discharge line 327, 335, 339 each terminate in the chambers. The feed lines 326, 332, 338 are connected via the valve assembly 350 to the oxygen-generating device so that the oxygen generated by the oxygen-generating device can selectively be conducted into one of the chambers 328, 351, 352 by means of the valve assembly. The discharge lines 327, 335, 339 are connected to a control device 320 for regulating flow, which is designed to supply oxygen, removed from the chambers 328, 351, 352, to a digestion reactor of the analysis device via gas line 313, and/or to a plurality of discontinuous consumers via the gas lines 321.

The axial movement of the piston 325, 333, 340 is instigated by the drives 341, 342, 343. The pressure predominating in the chambers 328, 351, 352 is always monitored by a pressure sensor 344, 348, 349. To fill a chamber 328, 351, 352 with oxygen, the respective piston 325, 333, 340 is retracted while enlarging the chamber volume; to empty the chamber 328, 351, 352, the piston 325, 333, 340 is, correspondingly, moved downwards towards the floor 324, 334, 337 while reducing the chamber volume.

The valve assembly 350, the control device 320 for regulating flow, and the drives 341, 342, 343 can be controlled by means of an electronic data processing device. The gas storage device 319 can possess a separate data processing device designed for this purpose. For communication, this can be connected to a control and regulating device of the analysis device in which the gas storage device 319 is inserted. Alternatively, the control device 320 for regulating flow can also be designed to control the valve assembly 350 and the drives 341, 342, 343. It is also possible for a central control and analysis device of the analysis device in which the gas storage device 319 is inserted to assume control of the valve assembly 350, control device 320 for regulating flow, and the drives 341, 342, 343. A method for storing oxygen in the gas storage device 319 and a method for operating the gas storage device 319 that always supplies the digestion reactor and other consumers, as needed, with oxygen is described below:

In a first work cycle (filling), a first cylinder—the cylinder 323 in the example portrayed in FIG. 3—is fed by the oxygen-generating system and filled with oxygen until a certain fill volume is reached. The particular fill volume is determined by a given axial position of the piston 325 and a given control pressure that predominates in the chamber 328. Once the particular fill volume is reached, the feed line 326 is closed by the valve assembly 350, in order to stop the transport of oxygen into the chamber 328. The valve assembly 350 can supply the stream of oxygen continuously generated by the oxygen device sequentially to the other chambers of the gas storage device 319 serving as storage volumes. In the example portrayed here, the second cylinder 331 has just been completely filled with the given maximum oxygen fill volume while the first cylinder 323 is being filled. A data processing device controlling the valve assembly 350 and drives 341, 342, 343 can control the filling of the cylinders 323, 331, 336 in a fully automated manner, based upon the measurement values supplied by the pressure sensors 344, 348, 349, and taking into account the axial position of the piston 325, 333, 340 or a path traveled by the piston 325, 333, 340. As mentioned, the control function can also be performed by the control and analysis device of the analysis device. To detect a path traveled by the piston 325, 333, 340, position sensors can be provided (not shown in FIG. 3), the measurement values of which are detected and processed by the data processing device. Alternatively, the data processing device can ascertain the path traveled by the piston 325, 333, 340 on the basis of the movement of the drives 341, 342, 343.

In a second work cycle (dosing), oxygen is removed from a filled chamber and fed to the digestion reactor of the analysis device and/or one or more other oxygen consumers according to the current need. In an example shown in FIG. 3, the third cylinder 336 is being operated in a second work cycle. For this purpose, a gas path or several gas paths between the chamber 352 and the consumers to be supplied with oxygen or the digestion reactor, are released by means of the control device 320 for regulating flow. By means of the drive 343, the piston 340 is moved toward the floor 337 of the chamber 352 and thus reduces the volume of the chamber 352. A regulated force is thereby exerted on the oxygen held in the chamber 352, which generates in the chamber an overpressure, dependent upon the force, that serves to transport a desired amount of oxygen to the digestion reactor, or to the other consumers. The drive 343 and the control device 320 can be controlled in this context by means of the aforementioned electronic data processing device, or by the control and analysis device of the analysis device, based upon the measurement values supplied by the pressure sensor 349, the path traveled by the piston 340 during dosing, and an amount of oxygen, specified by the control and analysis device, required for the current operating phase of the analysis device.

This makes it possible to provide the analysis device with a controlled amount of oxygen for performing the analytical process step. This can range from one or more portions of the amount of oxygen contained in the individual chambers 328, 351, 352 up to the entire storage volume of the gas storage device 319. It is also possible to couple several filled, individual storage volumes for a cumulative metering, such as a synchronized timing of filling and dosing work cycles of the individual cylinders serving as storage devices.

The invention claimed is:

1. An analysis device for the determination of a measurement variable, comprising:
    a digestion reactor having a gas inlet and a gas outlet;
    a measuring device connected to the gas outlet of the digestion reactor and embodied to record measurement values dependent upon the measurement variable, which is dependent upon the concentration of one or more constituents of a sample;
    a control and analysis device configured to receive and to process the measurement values;
    an oxygen-generating device embodied to generate oxygen; and
    a gas line system connecting the oxygen-generating device to the gas inlet of the digestion reactor to supply the oxygen generated by the oxygen-generating device to the digestion reactor, the gas line system including a gas storage device including a chamber having a variable volume that serves for receiving an amount of oxygen to be stored, wherein a gas feed line terminates in the chamber of the gas storage device and is connected to a gas outlet of the oxygen-generating device, and wherein the chamber includes a wall region designed to enlarge the volume of the chamber by deflecting against a restoring force when an amount of oxygen in the chamber increases.

2. The analysis device according to claim 1, wherein the gas line system further includes a control device for regulating the flow of an oxygen stream flowing through the gas line system to the digestion reactor.

3. The analysis device according to claim 2, wherein the chamber includes a gas outlet connected to the gas inlet of the digestion reactor via the control device for regulating flow.

4. The analysis device according to claim 3, wherein the gas line system additionally connects the oxygen-generating device via the gas storage device to at least one additional consumer to supply the at least one additional consumer with oxygen generated by the oxygen-generating device, and wherein the control device for regulating flow is additionally embodied to control a flow of oxygen through the gas line system from the gas storage device to the at least one additional consumer.

5. The analysis device according to claim 4, wherein the gas outlet of the chamber of the gas storage device is connected via the control device for regulating flow to each of the at least one additional consumer.

6. The analysis device according to claim 3, wherein the gas feed line terminating in the chamber of the gas storage device is connected to the gas outlet of the oxygen-generating device via a pump.

7. The analysis device according to claim 1, wherein the chamber is formed by a cylinder closed on one side by a floor, and a piston that is movably guided axially in the cylinder along a cylinder axis and seals the cylinder gas-tightly on the side of the cylinder opposite the floor, and wherein an axial position of the piston depends upon the amount of oxygen contained in the chamber.

8. The analysis device according to claim 7, wherein the gas line system includes a means for monitoring the axial position of the piston.

9. The analysis device according to claim 1, wherein the control and analysis device is further configured to control the analysis device to perform measurements for determining the measurement variable.

10. An analysis device for the determination of a measurement variable, comprising:
a digestion reactor having a gas inlet and a gas outlet;
a measuring device connected to the gas outlet of the digestion reactor and embodied to record measurement values dependent upon the measurement variable, which is dependent upon the concentration of one or more constituents of a sample;
a control and analysis device configured to receive and to process the measurement values;
an oxygen-generating device embodied to generate oxygen; and
a gas line system connecting the oxygen-generating device to the gas inlet of the digestion reactor to supply the oxygen generated by the oxygen-generating device to the digestion reactor, the gas line system including a gas storage device including at least two chambers, each chamber having a variable volume changeable by means of a control, wherein each chamber serves for receiving an amount of oxygen to be stored, wherein a gas feed line terminates in each of the chambers and is connected to the gas outlet of the oxygen-generating device, and wherein each of the at least two chambers includes a gas outlet connected to the gas inlet of the digestion reactor.

11. The analysis device according to claim 10, wherein each of the gas feed lines is connected via a valve assembly to the gas outlet of the oxygen-generating device, and wherein the valve assembly is designed to selectively block or release gas lines running from the gas outlet of the oxygen-generating device to the at least two chambers alternatingly or according to a sequence specified by the control.

12. The analysis device according to claim 11, wherein the at least two chambers are each formed by a cylinder closed on one side by a floor, and a piston that is moveably guided axially in the cylinder along a cylinder axis and seals the cylinder gas-tightly on the side of the cylinder opposite the floor, and wherein each piston is connected to a drive that is embodied to produce an axial movement of the piston.

13. The analysis device according to claim 12, wherein the drive to which the piston is connected is actuatable by the control.

14. The analysis device according to claim 12, wherein the gas line system includes a means for monitoring the axial position of the piston.

15. The analysis device according to claim 11, wherein the gas line system further includes a control device for regulating the flow of an oxygen stream flowing through the gas line system to the digestion reactor, wherein the gas outlets of the at least two chambers are connected via the control device to the gas inlet of the digestion reactor, wherein the control and analysis device is further configured to control the analysis device including the control device, the valve assembly, and/or the volume of the at least two chamber of the gas storage device, and wherein the control and analysis device is further configured to perform measurements for determining the measurement variable.

16. The analysis device according to claim 10, wherein the gas line system further includes a control device for regulating the flow of an oxygen stream flowing through the gas line system to the digestion reactor.

17. The analysis device according to claim 16, wherein the gas outlet of each of the at least two chambers is connected to the gas inlet of the digestion reactor via the control device for regulating flow.

18. The analysis device according to claim 17, wherein a gas feed line terminates in each chamber of the gas storage device and is connected to a gas outlet of the oxygen-generating device via a pump.

19. The analysis device according to claim 17, wherein the gas line system additionally connects the oxygen-generating device via the gas storage device to at least one additional consumer to supply the at least one additional consumer with oxygen generated by the oxygen-generating device, and wherein the control device for regulating flow is additionally embodied to control a flow of oxygen through the gas line system from the gas storage device to the at least one additional consumer.

20. The analysis device according to claim 19, wherein the gas outlet of the each of the at least two chambers of the gas storage device is connected via the control device for regulating flow to each of the at least one additional consumer.

21. A method for automatically determining a measurement variable of a sample in a digestion reactor, comprising:
continuously generating a constant amount of oxygen per time unit using an oxygen-generating device;
transporting the generated oxygen into a gas storage device having at least one chamber with a variable volume, the at least one chamber embodied to receive the generated oxygen to be stored;
removing a currently-required amount of oxygen from the gas storage device and transporting the currently-required oxygen to a digestion reactor, and/or to one or more additional consumers;
performing a digestion of the sample in the digestion reactor, and introducing into the digestion reactor the currently-required oxygen;
recording a measurement value dependent upon the measurement variable in a gas stream discharged from the digestion reactor; and
transporting the generated oxygen into the at least one chamber, wherein a wall region of the at least one chamber is deflected against a restoring force when the amount of oxygen contained in the at least one chamber increases while enlarging the volume of the at least one chamber, such that a volume of the generated oxygen that depends upon a delivery rate with which the generated oxygen is transported is stored in the at least one chamber under a pressure determined by the restoring force.

22. The method according to claim 21, wherein the at least one chamber of the gas storage device is formed by a cylinder closed on one side by a floor, and a piston that is axially movable in the cylinder along the cylinder axis and seals the cylinder gas-tightly on the side of the cylinder opposite the floor, and wherein the generated oxygen is transported into the chamber at a delivery rate such that a volume of the generated oxygen that depends upon the delivery rate is stored in the chamber under a pressure determined by the weight of the piston and cross-section of the cylinder.

23. The method according to claim 22, wherein the removal of the currently-required amount of oxygen is controlled and/or regulated on the basis of an axial position of the piston.

24. The method according to claim 21, wherein the transporting of the generated oxygen into the at least one chamber is effected using a pump.

25. A method for automatically determining a measurement variable of a sample in a digestion reactor, the method comprising:
continuously generating a constant amount of oxygen per time unit using an oxygen-generating device;
transporting the generated oxygen into a gas storage device including at least two chambers, each chamber having a variable volume changeable by means of a control, wherein each chamber serves for receiving an amount of oxygen to be stored, wherein the generated oxygen is transported into a first of the at least two chambers while enlarging the volume of the first chamber until a given volume and a given control pressure are reached in the first chamber;
after the given volume and given control pressure in the first chamber are reached, removing a currently-required amount of oxygen from the first chamber and transporting the currently-required amount of oxygen to a digestion reactor and/or to one or more additional consumers;
performing a digestion of the sample in the digestion reactor and introducing into the digestion reactor the currently-required amount of oxygen; and
recording a measurement value dependent upon the measurement variable in a gas stream discharged from the digestion reactor.

26. The method according to claim 25, wherein the oxygen generated by the oxygen-generating device is transported into a second chamber of the at least two chambers during the removal of the currently-required amount of oxygen from the first chamber.

* * * * *